(12) United States Patent
Kanamaru et al.

(10) Patent No.: US 7,811,524 B2
(45) Date of Patent: Oct. 12, 2010

(54) REACTOR, REACTOR CONTROL SYSTEM, AND CATALYTIC GAS PHASE OXIDATION REACTION METHOD

(75) Inventors: Takashi Kanamaru, Yokkaichi (JP); Shuhei Yada, Yokkaichi (JP); Kimikatsu Jinno, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 806 days.

(21) Appl. No.: 11/597,822

(22) PCT Filed: Dec. 1, 2004

(86) PCT No.: PCT/JP2004/018231

§ 371 (c)(1),
(2), (4) Date: Mar. 23, 2007

(87) PCT Pub. No.: WO2005/115606

PCT Pub. Date: Dec. 8, 2005

(65) Prior Publication Data

US 2008/0025879 A1    Jan. 31, 2008

(30) Foreign Application Priority Data

May 27, 2004   (JP)  ............................. 2004-158036

(51) Int. Cl.
*G05D 23/00*     (2006.01)
(52) U.S. Cl. ........................ 422/109; 422/201
(58) Field of Classification Search ............... 422/201
See application file for complete search history.

(56) References Cited

U.S. PATENT DOCUMENTS

| 2,098,148 | A | * | 11/1937 | Jarl | ............................. 422/201 |
| 3,482,948 | A | * | 12/1969 | Miegel | ....................... 422/197 |
| 2004/0247500 | A1 | * | 12/2004 | Ashe et al. | ................... 422/201 |

FOREIGN PATENT DOCUMENTS

| JP | 54 21966 | 2/1979 |
| JP | 2001 280774 | 10/2001 |
| JP | 2004-26799 | 1/2004 |

* cited by examiner

*Primary Examiner*—Walter D Griffin
*Assistant Examiner*—Timothy Cleveland
(74) *Attorney, Agent, or Firm*—Oblon, Spivak, McClelland, Maier & Neustadt, L.L.P.

(57) ABSTRACT

A multi-tubular reaction apparatus, a control system, and a method are provided for controlling temperature change of a heat medium in the reaction apparatus, and quickly adjusting fluctuation in temperature, to thereby properly control a reaction. In particular, the apparatus and system apply to a catalytic gas-phase oxidation reaction such as in producing (meth)acrylic acid or the like. The reaction apparatus includes a multi-tubular reactor having a plurality of reaction tubes in a shell in which a heat medium circulates, and a heat medium cooling apparatus outside the reactor. The reaction apparatus includes a process for primarily cooling the heat medium taken out outside the shell, a process for secondarily cooling a part of the primarily cooled heat medium, and a line for enabling the secondarily cooled heat medium and the primarily cooled heat medium, which is not secondarily cooled, to circulate in the shell.

5 Claims, 8 Drawing Sheets

REACTOR, REACTOR CONTROL SYSTEM, AND CATALYTIC GAS PHASE OXIDATION REACTION METHOD

TECHNICAL FIELD

The invention relates to a multi-tubular reaction apparatus and a control system for the same, the multi-tubular reaction apparatus being capable of controlling change in temperature of a heat medium, quickly adjusting fluctuation in temperature, and thereby, properly performing a reaction, particularly, a multi-tubular reaction apparatus and a control system for the same, the multi-tubular reaction apparatus being capable of preventing a runaway reaction or early deterioration of a catalyst in producing (meth)acrylic acid or the like from propane, propylene or isobutylene in a catalytic gas-phase oxidation method, for example, so as to stably produce the above with a high yield for a long term, the multi-tubular reaction apparatus being properly applicable to a catalytic gas-phase oxidation reaction.

BACKGROUND ART

In the case of producing a compound in a catalytic gas-phase oxidation method such as a case of producing (meth)acrylic acid or the like from propane, propylene or isobutylene, a multi-tubular reaction apparatus has been conventionally used (refer to JP-A-2004-26799, for example). A usual multi-tubular reactor has a structure in which plural reaction tubes filled with a catalyst and plural baffle plates having an opening for spreading a heat medium led in a shell of the reactor all over the shell are interiorly provided in the shell of the reactor. In controlling an operation of the multi-tubular reactor, a temperature of the heat medium flowing in the shell is detected so that the temperature of the heat medium in the shell would be controlled to be uniform on the basis of a result of the detection, generally.

As a method for controlling the temperature of the heat medium to be uniform, generally adopted is a method in which a part of the heat medium is taken out outside the reactor, cooled so that the temperature of the heat medium at a predetermined measuring point, an outlet of a heat medium circulation pump, for example, would be constant, and then, returned to the reactor. In this case, it is required to control the external circulation flow of the heat medium when the cooling load is set to be constant while the cooling load of the heat medium should be controlled when the external circulation flow is set to be constant to the contrary.

There are problems, however, such that a runaway reaction is likely to be caused due to cooling not in time and that a hot spot is likely to cause a life of the catalyst to be deteriorated when the circulation amount is low and the reaction temperature rises in the case of changing the external circulation amount since the catalytic gas-phase oxidation reaction as described above is generally a largely exothermic reaction.

Further, in the case of changing the cooling load, control is carried out through many steps as follows. That is, the amount of cooling water in a heat exchanger is changed in accordance with an indication of a temperature controller, the change is transmitted to the heat medium, the heat medium is further fed to the heat medium circulation pump, and then, a temperature at a measuring point is changed. Accordingly, time delay in the control occurs easily, and thereby, so called overshoot, in which actual temperature changes, exceeding the set temperature, easily happens. This causes a problem of unstableness.

DISCLOSURE OF THE INVENTION

An object of the invention is to provide a multi-tubular reaction apparatus and a control system for the same, the multi-tubular reaction apparatus being capable of solving the above conventional problems, controlling change in temperature of a heat medium, quickly adjusting fluctuation in temperature and properly performing a reaction and to provide a multi-tubular reaction apparatus and a control system for the same, the multi-tubular reaction apparatus being properly applicable to a catalytic gas-phase oxidation reaction in the case such as producing (meth)acrylic acid or the like from propane, propylene or isobutylene.

For the purpose of achieving the above objects, the invention is to provide the following reaction apparatus, a reaction apparatus control system and a catalytic gas-phase oxidation reaction method.

(1) A reaction apparatus comprising: a multi-tubular reactor, which comprises a shell and a plurality of reaction tubes provided in the shell and filled with a catalyst, and in which a heat medium circulates in the shell; and a cooling apparatus for the heat medium, the cooling apparatus provided outside the reactor, the reaction apparatus characterized by comprising: a process for primarily cooling at least a part of the heat medium taken out outside the shell; a process for secondarily cooling a part of the primarily cooled heat medium; and a line for enabling the secondarily cooled heat medium and a residual part of the primarily cooled heat medium, which is not secondarily cooled, to circulate in the shell.

(2) A reaction apparatus control system in the reaction apparatus according to the above (1), the reaction apparatus control system characterized by adjusting a temperature of the heat medium circulating in the shell by adjusting the flow of the secondarily cooled heat medium and the flow of the residual part of the primarily cooled heat medium, which is not secondarily cooled, on the basis of a temperature at at least one point selected from a heat medium temperature on the shell side and a catalyst temperature.

(3) The reaction apparatus control system according to the above (2), characterized in that a flow control valve provided in a line for supplying at least a part of the primarily cooled heat medium to the secondarily cooling process and a flow control valve provided in a line of the primarily cooled heat medium, which is bypassed without supplied to the secondarily cooling process, are operated in an opposite direction in adjusting a temperature of the heat medium circulating in the shell.

(4) A catalytic gas-phase oxidation reaction method characterized by using the reaction apparatus according to the above (1) and performing a catalytic gas-phase oxidation reaction by controlling a temperature by means of the reaction apparatus control system according to the above (2) and (3) in the reaction apparatus.

(5) A system for controlling a reaction apparatus comprising: a multi-tubular reactor, which comprises a shell and a plurality of reaction tubes provided in the shell and filled with a catalyst, and in which a heat medium circulates in the shell; and at least one cooling apparatus for the heat medium, the cooling apparatus provided outside the reactor, the system for controlling a reaction apparatus characterized in that a flow control valve provided in a line for supplying at least a part of the heat medium having been taken out outside the shell to the cooling apparatus for the heat medium and a flow control valve provided in a line of the heat medium, which is bypassed without supplied to the cooling apparatus for the heat medium, are used for adjusting a temperature of the heat medium circulating in the shell.

The essence of a reaction apparatus in accordance with the invention is to be characterized in that a heat medium taken out outside a shell is once cooled to a reference temperature, that a part of the heat medium cooled to the reference temperature is further cooled (by reducing the flow so as to easily control the temperature) and that the heat medium cooled to the reference temperature is mixed with the heat medium further cooled under good temperature control. Using the reaction apparatus allows the heat medium to be highly precisely controlled in temperature. The precision necessary to the temperature control required in the case such as producing (meth)acrylic acid from propane, propylene or isobutylene is typically 0.2 to 1° C. It is quite difficult to control a temperature of the heat medium, which is massively circulated, in one step with such a precision. Nevertheless, the apparatus in accordance with the invention enables control with such a precision.

In the reference numerals and signs in the drawings, 1 denotes a shell, 2 denotes a circulation pump, 3 and 4 denote a heat exchanger, 5 denotes a temperature controller (TC), 6 denotes an A valve, 7 denotes a B valve, L1 denotes a pipe, L2 denotes a discharging tube, L3 denotes a discharging tube, L4 denotes a path of flow for circulation, L5 denotes a path of flow for circulation, L6 denotes a heat medium supplying tube and L7 denotes a pipe.

BEST MODE FOR CARRYING OUT THE INVENTION

The invention will be described in detail on the basis of FIGS. 1 to 3. A mode of the invention is, however, not limited to what is shown in the drawings.

Figure 1:
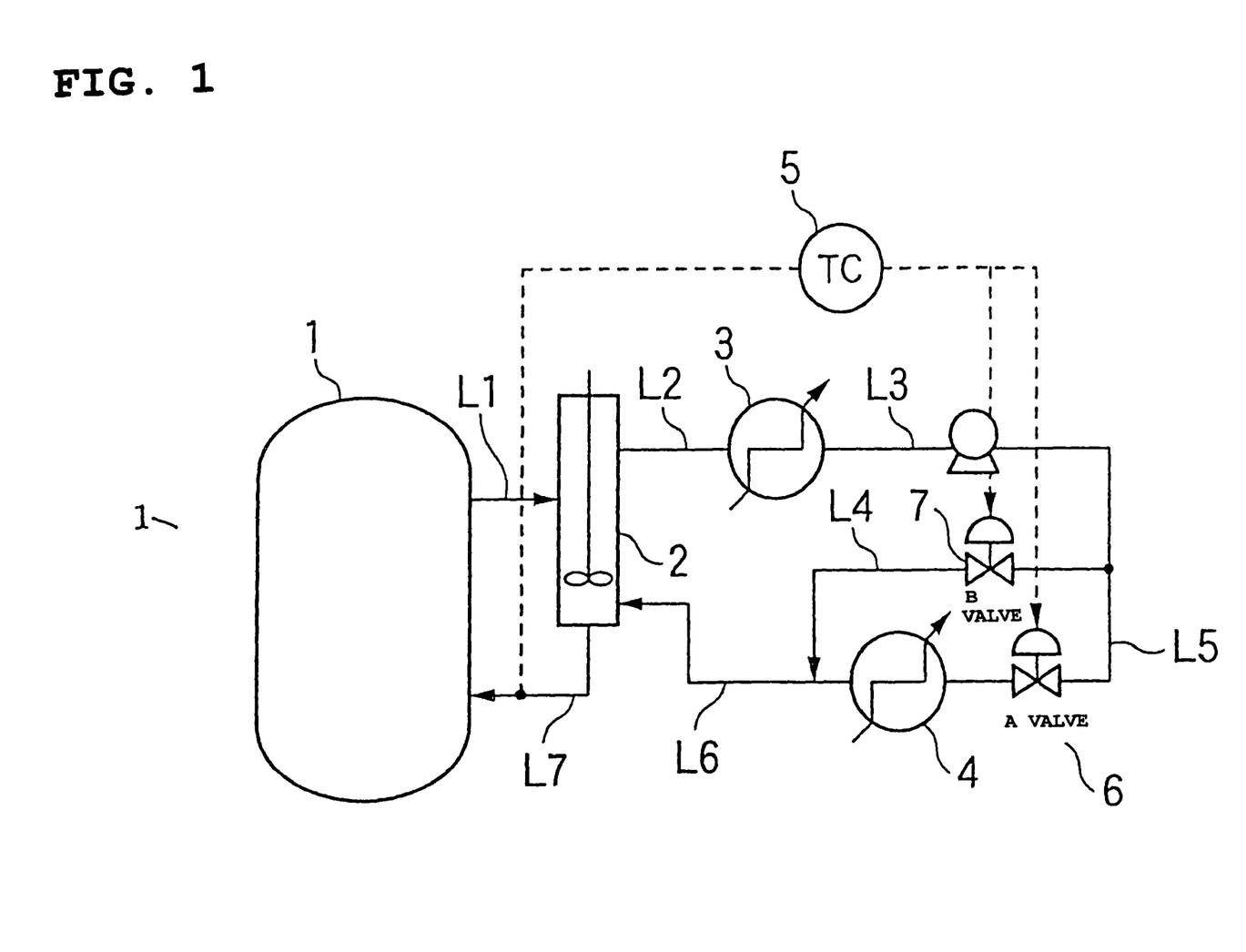
FIG. 1 shows an example of a reaction apparatus and a system for controlling temperature of a heat medium in accordance with the invention.

FIG. 1 shows an example of a reaction apparatus in accordance with the invention. In FIG. 1, 1 denotes a shell of a multi-tubular reactor. In the shell, a plurality of reaction tubes (omitted from the drawings) filled with a catalyst are fixed by means of both of lower tube plate and an upper tube plate (omitted from the drawings) so as to be interiorly provided. The shell is provided on its upper and lower ends with inlet and outlet pathes (omitted from the drawings) for gas used as a raw material in a reaction. The raw material gas circulates in the reaction tube in a rising or falling flow direction. The flow direction of the raw material gas is not particularly limited, but the rising flow is preferable.

The shell 1 is also provided with a pipe L7 for leading a heat medium. A heat medium increased in pressure by means of a circulation pump 2 is led through the pipe L7 into the shell 1. The heat medium led into the shell 1 rises with its flow direction changed by means of a baffle plate interiorly mounted in the shell 1 while the heat medium contacts with an outer surface of the reaction tube to absorb reaction heat, and then, it returns to the circulation pump 2 through a pipe L1 provided in the shell 1.

A part of the heat medium having absorbed the reaction heat is taken out from a discharging tube L2 provided in an upper part of the circulation pump 2 and cooled by means of a heat exchanger 3 (primary cooling). After that, it is divided to paths of flow for circulation L4 and L5 at an optional rate according to necessity in response to operations of an A valve 6 and a B valve 7, which are mentioned later, and then, the heat medium divided to the path of flow for circulation L5 is further cooled by means of a heat exchanger 4. Two heat medium flows different in temperature (a heat medium flow at a high temperature, which has only undergone the primary cooling, and a heat medium flow at a low temperature, which has undergone the primary cooling and secondary cooling) are formed as described above and mixed to be inhaled into the circulation pump 2 through a heat medium supplying tube L6 again to be led into the shell 1.

The flow of the two heat medium flows different in temperature is controlled by means of the A valve 6 (a low temperature heat medium flow control valve) and the B valve 7 (a high temperature heat medium flow control valve) which operate in accordance with an indication of a temperature controller (TC) 5. In the control, the A valve 6 and the B valve 7 are preferably arranged to operate in an opposite direction. That is to say, in a control system of the temperature controller (TC) 5, the A valve 6 and the B valve 7 (the left-hand illustration) and in an illustration showing a relation between an output and a valve opening (the right-hand illustration), which are shown in FIG. 2, opening and closing operations of the A valve 6 and the B valve 7 are preferably arranged to be carried out in a opposite direction with respect to a controlling output of the TC, as shown in the illustration showing a relation between an output and a valve opening. At that time, more concretely, the controlling output (MV) is lowered to carry out an operation for setting a measured temperature (PV) to accord to a set temperature (SV) in the case that the PV is higher than the SV while the A valve 6 is set to be moved in an opening direction and the B valve 7 is set to be moved in a closing direction in order to increase a cooling load in accordance with a change of the MV. The A valve 6 is fully opened and the B valve 7 is fully closed when the MV is 0% while, on the contrary, the B valve 7 is fully opened and the A valve 6 is fully closed when the MV is 100% so that an operation of the control valve would correspond to the MV. As described above, a characteristic of the invention is to divide the heat medium taken out from the shell 1 into two kinds of flow of a high temperature and a low temperature to continuously vary a mixture ratio therebetween so as to control a reaction temperature precisely without changing an amount of circulation of the heat medium.

Driving a plurality of control valves (usually two valves) by means of one controlling output is, per se, a well-known matter. For such driving, generally performed is so-called split control (refer to FIGS. 3A and 3B). In the control, there are two kinds of controlling method, one of which is V characteristic control (refer to FIG. 3(A); combining valves having opposite characteristics) and the other of which is parallel characteristic control (refer to FIG. 3(B); combining valves having a same characteristic).

In the invention, the flow of two kinds of fluid having opposite natures of high and low temperatures is controlled to control a temperature as described above. In such a case, typically performed is the V characteristic control shown in FIG. 3(A). In the above control method, however, a runaway reaction is likely to be caused due to cooling not in time or a hot spot is likely to cause a life of the catalyst to be deteriorated when the heat medium circulation amount is lowered with a controlling output of around 50% and the reaction temperature rises, since the catalytic gas-phase oxidation reaction, which is claimed in the invention, is a largely exothermic reaction.

Figure 2:
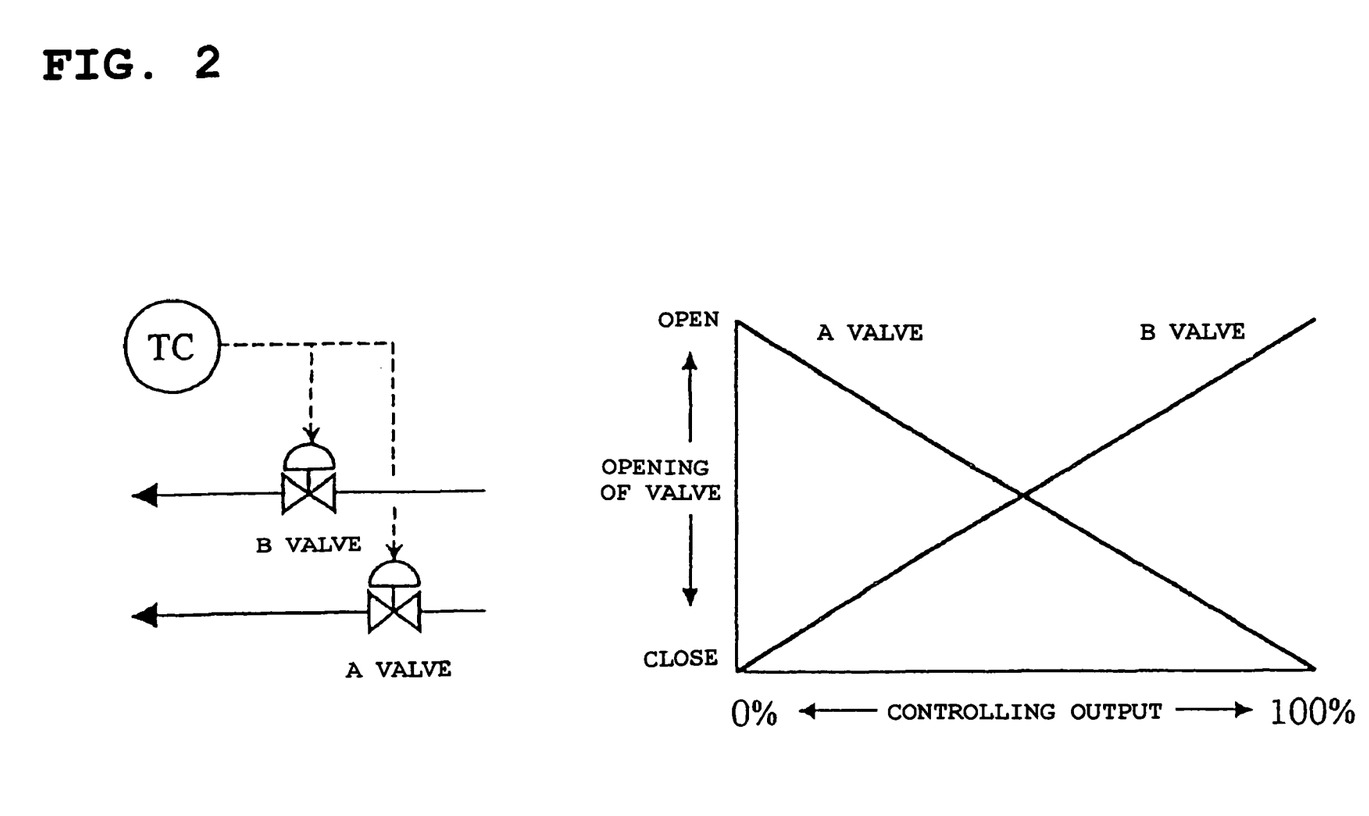
FIG. 2 is a conceptual view of heat medium flow control preferably performed in the invention.
Figure 3A:
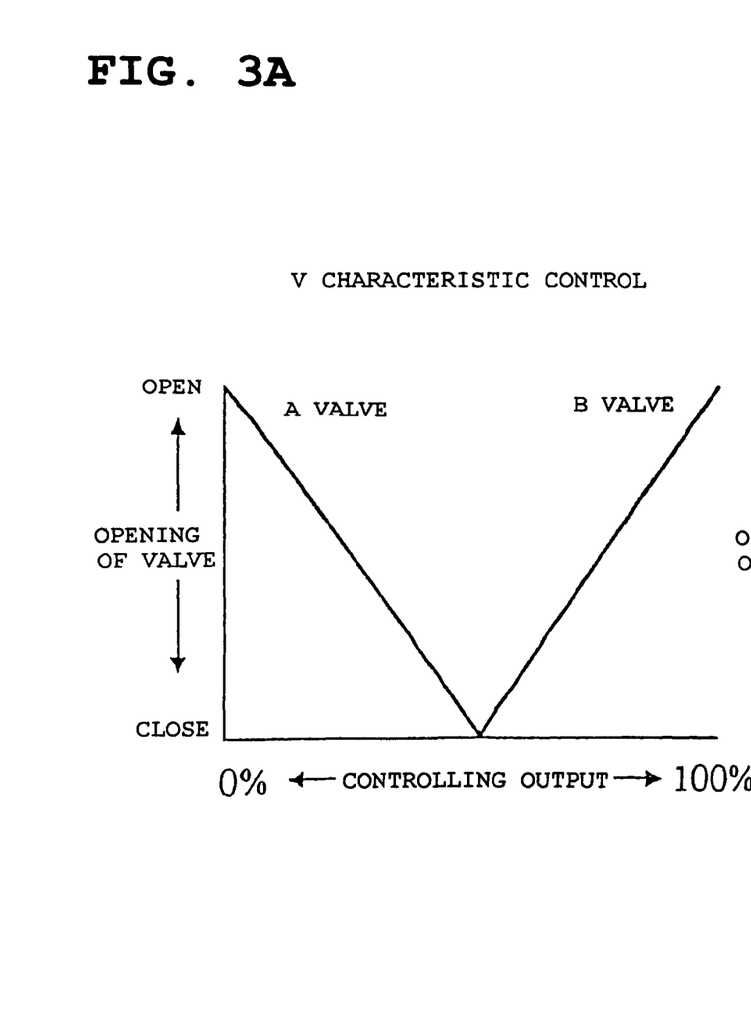
FIGS. 3A and 3B are conceptual views of split control generally performed.
Figure 3B:
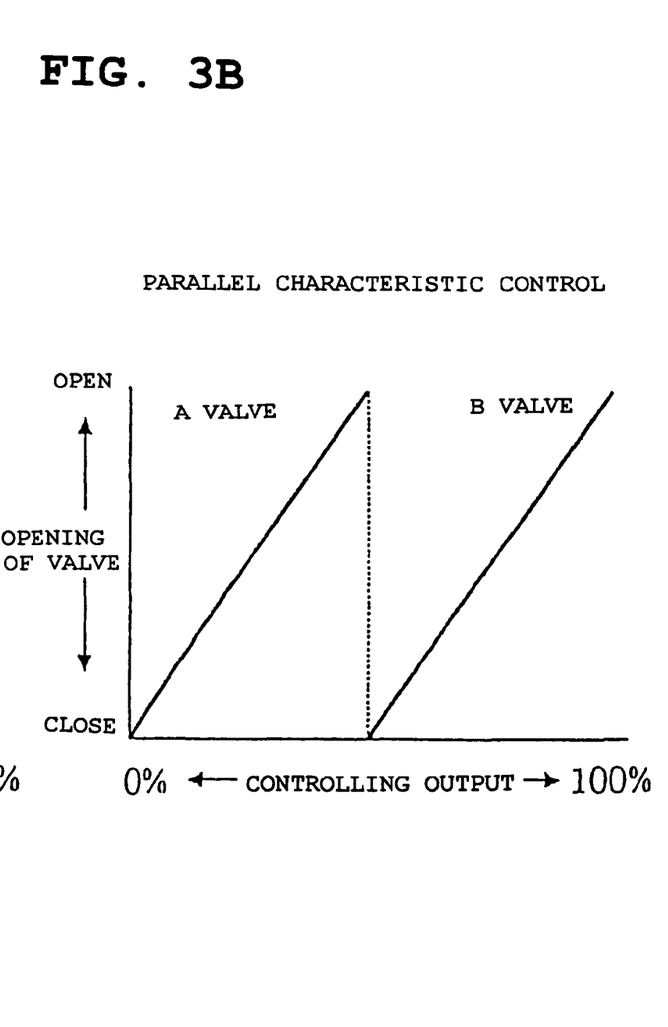

Contrary to the typical controlling method described above, the controlling method according to the invention, which is shown in FIG. 2, is characterized in that it is possible to rapidly follow the change in reaction temperature since the heat medium circulation amount is not changed and that overshoot in controlling does not occur, and thereby, a temperature of the reactor can be quickly adjusted.

The controller used in the invention is for stably maintaining a reaction temperature, and therefore, a temperature of a reactor is used as an input. The temperature of a reactor is different, depending on difference in flow speed of the raw material gas or the heat medium or in filling condition of a catalyst or location of a measuring point. Accordingly, a specific measuring point is representatively used for the control in many cases. For a temperature measuring location of a reactor, selected is or are any one or both of a point in the heat medium on the shell side and a catalyst filling layer in the reaction tube. The temperature of the heat medium on the shell side is generally measured at an outlet L7 or an inlet L1 of the circulation pump 2. The temperature in the shell or in circulation paths L2 to L6 can be also referred to effectively. Further, it is better to measure a temperature of a plurality of reaction tubes rather than to measure at a single measuring point in measuring a temperature of a catalyst filling layer in the reaction tube. The measuring location (a distance from an inlet of the reaction tube) is also preferably changed in measuring so that temperature distribution of the reaction tube in a direction of an axis of the tube can be measured.

In the case that there is one temperature measuring point, usual feedback control by means of a PID controller is carried out so that the opening of the A valve and the B valve would be controlled to adjust a temperature of a reactor. When the reaction temperature is difficult to be stabilized with the feedback control, it is preferable to perform feedforward control in which a flow of a raw material, a temperature of air and such are taken into account together with a measured temperature. At that time, it is further preferable to input the temperature at plural measuring points for calculation as described above so as to obtain a controlling output.

As a valve used for controlling the flow in the invention, any valve such as a glove valve and a butterfly valve can be used without a trouble so long as it can change the passing flow continuously from a closing condition to an opening condition.

As a heat medium, a well-known heat medium in the multi-tubular reaction apparatus can be properly selected in accordance with necessity. The reaction apparatus control system in accordance with the invention, however, can be preferably applied in the case that a high temperature heat medium, which easily causes malfunction of the control valve, such as niter, which is a mixture of inorganic salt, and phenyl ethers organic liquid is used.

Composition of niter is exemplified as follows. That is to say, $KNO_3$ (potassium nitrate) of 53 weight %, $NaNO_2$ (sodium nitrite) of 40 weight % and $NaNO_3$ (sodium nitrate) of 7 weight %. A melting point of the mixture changes when the weight composition is changed to be different from the above. The composition of niter and permissible range thereof depend on a temperature condition for using niter.

For $KNO_3$ (potassium nitrate), $NaNO_2$ (sodium nitrite) and $NaNO_3$ (sodium nitrate), preferably used are industrial products respectively with purity of 95 weight % or more. This is because of tendency that a difference from the melting point designed as a mixture becomes large when the purity is less than 95 weight %.

In the invention, a well-known multi-tubular rector can be properly used as a multi-tubular reactor per se so long as it comprises a shell and plural reaction tubes, which are provided in the shell and filled with a catalyst, and it has a structure in which a heat medium circulates in the shell.

Further, the invention is preferably applied to a largely exothermic catalytic gas-phase oxidation reaction in producing (meth)acrylic acid from propane, propylene or isobutylene, for example, as described above, although it does not limit a reaction to be applied.

EXAMPLES

The invention will be further concretely described hereinafter on the basis of examples of experiments, but is not limited to the following examples of experiments.

Example 1

A composite compound in the following composition formula was used as a catalyst:

$Mo_{12}BiNi_3Co_{0.6}Fe_7Na_{0.1}B_{0.2}K_{0.1}Si_{18}O_X$ (The added numbers in the composition formula indicate composition of constitution elements (an atomic ratio) and the composition x of oxygen is a value determined in accordance with an oxidation state of respective metals.)

The composite compound in the above composition formula was produced according to JP-A-63-54942 to obtain a catalyst in a powder state. The catalyst was formed into a ring shape whose outer diameter is 5 mmΦ, whose inner diameter is 2 mmΦ and whose height is 4 mm.

Moreover, a multi-tubular reactor having 10,000 reaction tubes, which are 3,500 mm long, whose inner diameter is 25.4 mmΦ and which are made of stainless steel, and a shell whose inner diameter is 4,500 mmΦ was used. On the shell side of the reactor, alternately provided at regular intervals are a disk-shaped baffle plate and a doughnut-shaped baffle plate, which have an opening ratio of 18%.

Each of the reaction tubes was filled with the catalyst of 1.5 L and a raw material gas in which propylene concentration was 9 volume %, oxygen in a molecule state was 14.5 volume %, water was 9 volume % and nitrogen was 67.5 volume % was supplied from the lower part of the reactor under a gauge pressure of 75 kPa.

A temperature of a heat medium was adjusted on the basis of FIG. 1. As the heat medium, used was molten salt niter, which was a nitrate salt mixture in the above composition. The heat medium was circulated by means of a circulation pump 2 and the circulation flow was adjusted so that the difference in temperature between an outlet and inlet of a shell 1 would be 4° C. An input signal to a PID temperature controller (TC) 5 for controlling a temperature in reaction was taken out from a temperature detector (not shown) provided in an outlet piping L7 of the circulation pump 2.

A part of the heat medium was taken out from a discharging tube L2 to be cooled by means of a heat exchanger 3 in order to keep a temperature of the heat medium constant. An outlet line L3 of the heat exchanger 3 was divided into a line L5 for further cooling the heat medium by means of a heat exchanger 4 and a line L4 for bypassing the heat exchanger 4. The lines L4 and L5 were provided with valves for controlling the flow. The heat medium passed through the lines L4 and L5 at an optional rate. One heat medium passing through the L5 was further cooled by means of the heat exchanger 4, and then, joined with the other heat medium to return to the outlet of the circulation pump from L6.

An A valve 6 and a B valve 7 were arranged to operate in an opposite direction with respect to an output from the TC, as shown in FIG. 2.

In the Example, a raw material feed amount and an air temperature were simultaneously measured together with an input signal of the TC to perform feedforward control for calculating a control output MV of the TC on the basis of the inputted value.

Figure 4:
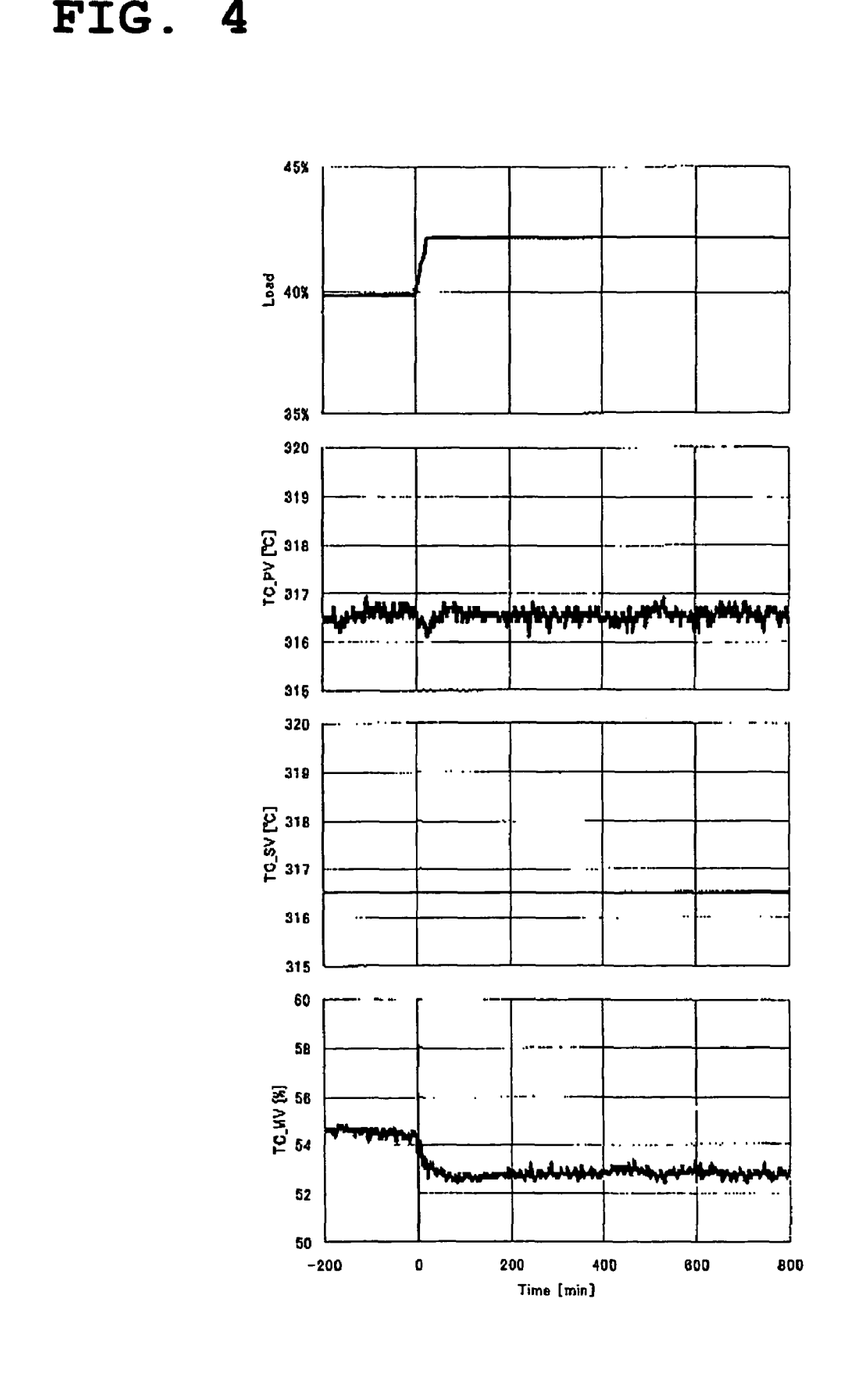
FIG. 4 shows operation data in Example 1.

After continuously carrying out for 24 hours an operation for adjusting a process under the above-mentioned condition, an operation load was increased by 2.4% in 20 minutes. A temperature of the heat medium (PV) was hardly fluctuated. FIG. 4 shows response of the TC at that time. In FIGS. 4 to 7, the operation load was shown by a ratio (%) of the raw material feed amount in practice to an upper limit of the feed amount.

Example 2

Figure 5:
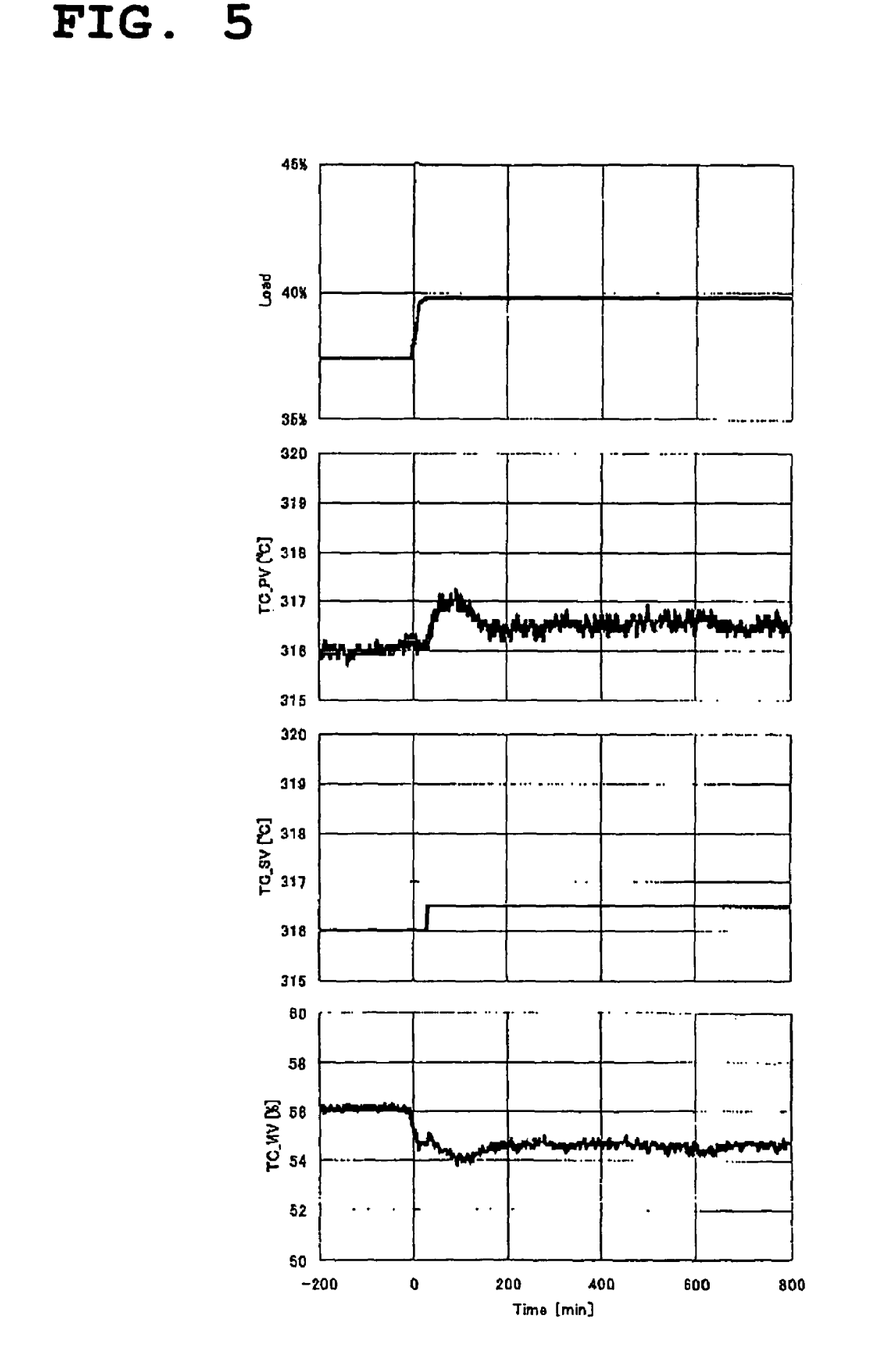
FIG. 5 shows operation data in Example 2.

The example was carried out similarly to Example 1 except that compensation by means of the raw material feed amount and the air temperature was reduced (weight in weighting the strength of influence was decreased). The operation was performed mainly with feedback control on the basis of a measured value of a heat medium temperature. In addition to change of the operation load, the SV was raised by 0.5° C. after 30 minutes from the change for the purpose of adjusting the reaction temperature, so that there was a change of around 1° C. in PV. The change in PV was, however, concluded within 200 minutes and the following capability to the change in SV was also good. Response of the TC at that time is shown in FIG. 5.

Example 3

Figure 6:
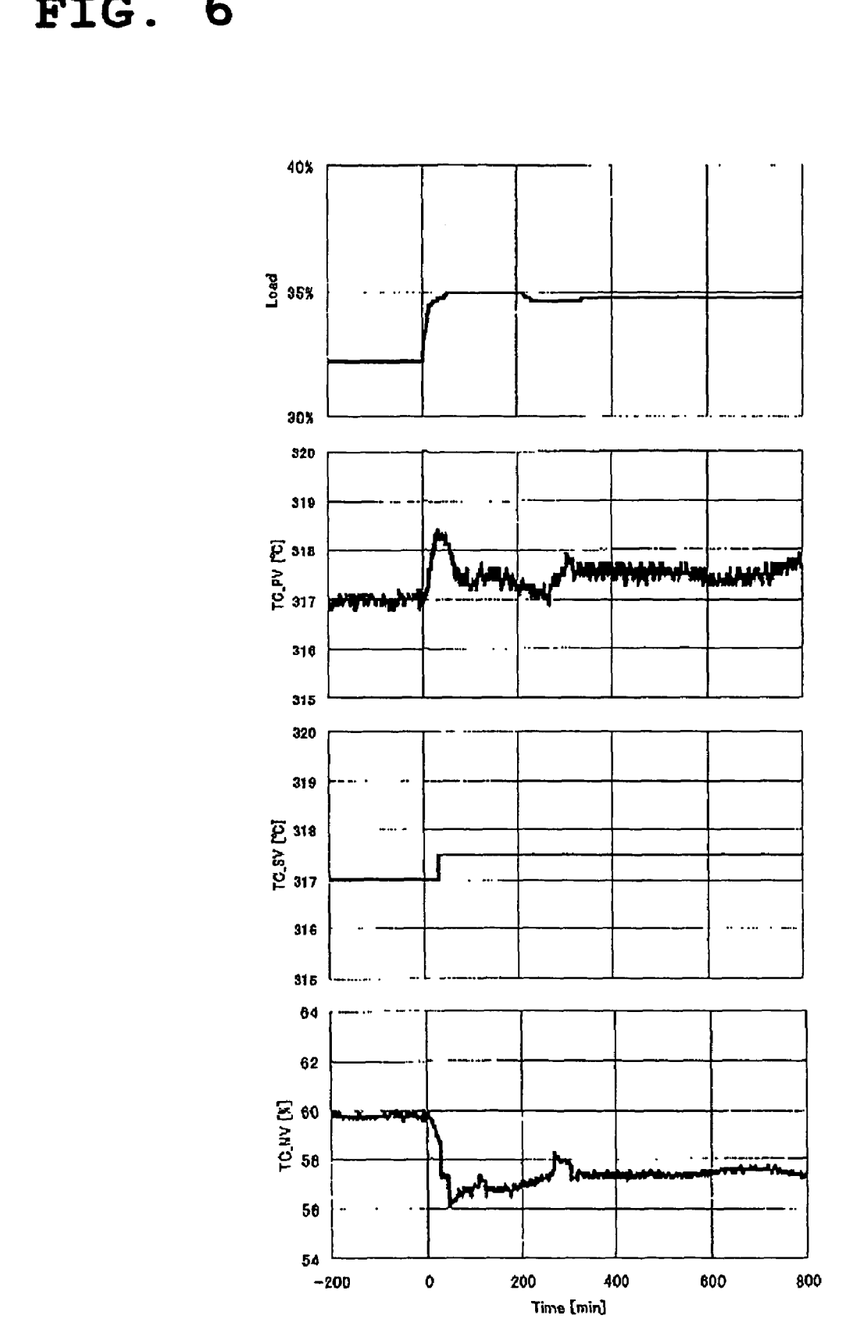
FIG. 6 shows operation data in Example 3.

The example was carried out similarly to Example 1 except that compensation by means of the raw material feed amount and the air temperature was not performed and that the feedback control was only carried out on the basis of a measured value of a heat medium temperature inputted to the TC. The SV was raised by 0.5° C. after 30 minutes from change of the operation load for the purpose of adjusting the reaction temperature, so that there was a change of around 1.3° C. in PV. The change in PV was, however, concluded in about 100 minutes and the following capability to the change in SV was also good. Response of the TC at that time is shown in FIG. 6.

Example 4

Figure 7:
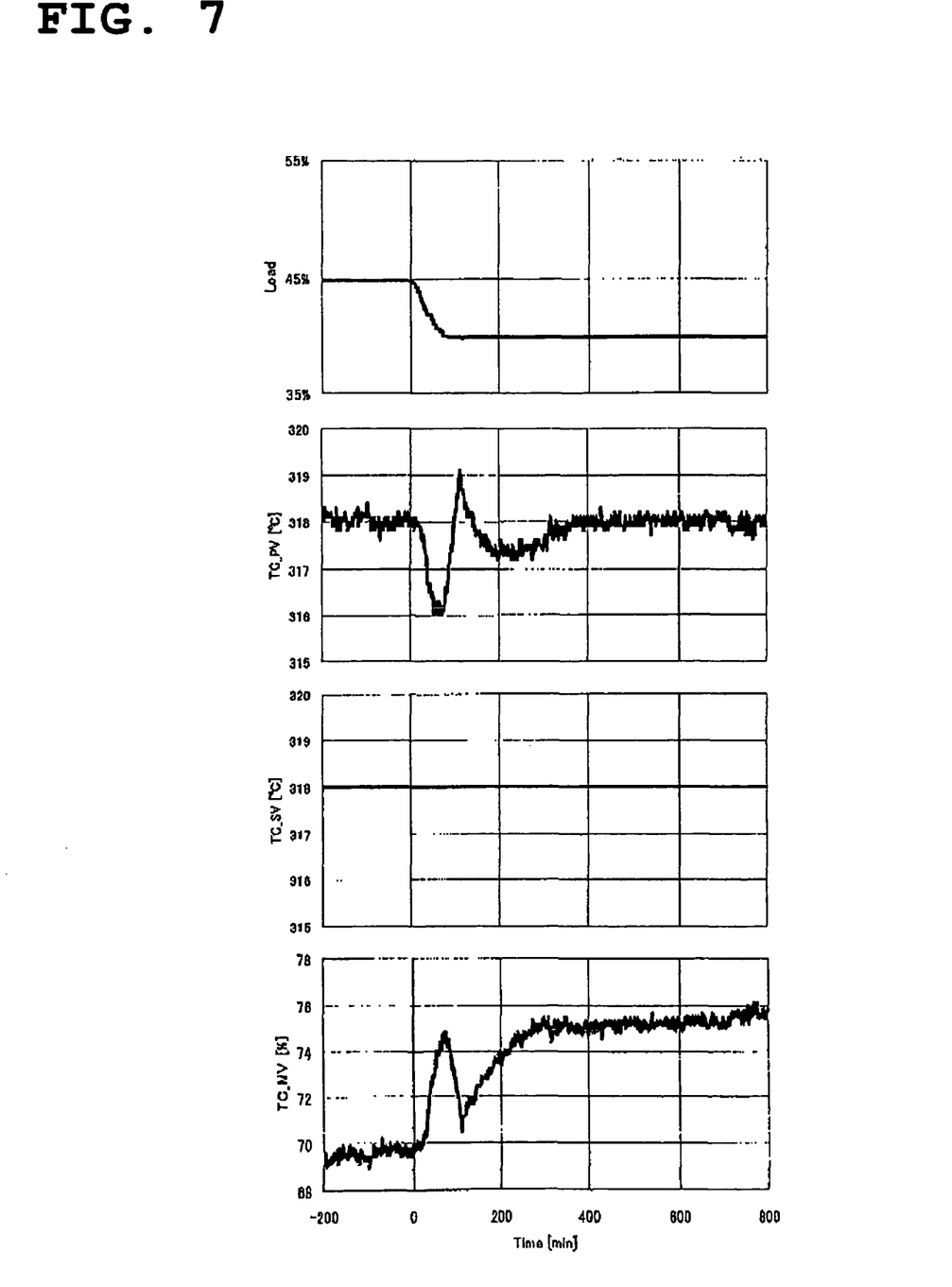
FIG. 7 shows operation data in Example 4.

The example was carried out similarly to Example 1 except that an output from the TC only controls the B valve and that the opening of the A valve is fixed at 50%. The operation of the TC was performed only with feedback control on the basis of a measured value of a heat medium temperature. In changing the operation load, the SV did not change while the PV changed by around 3° C. and the change in PV required 400 minutes for conclusion. Response of the TC at that time is shown in FIG. 7. Stability in control in the example was inferior to that of Examples 1 to 3 since the opening of the A valve was not controlled. Nevertheless, it can be seen that the temperature controlling method in this embodiment allows the temperature to be stably controlled.

While the invention has been described in detail and with reference to specific embodiments thereof, it will be apparent to one skilled in the art that various changes and modifications can be made therein without departing from the spirit and scope thereof.

Figure 8:
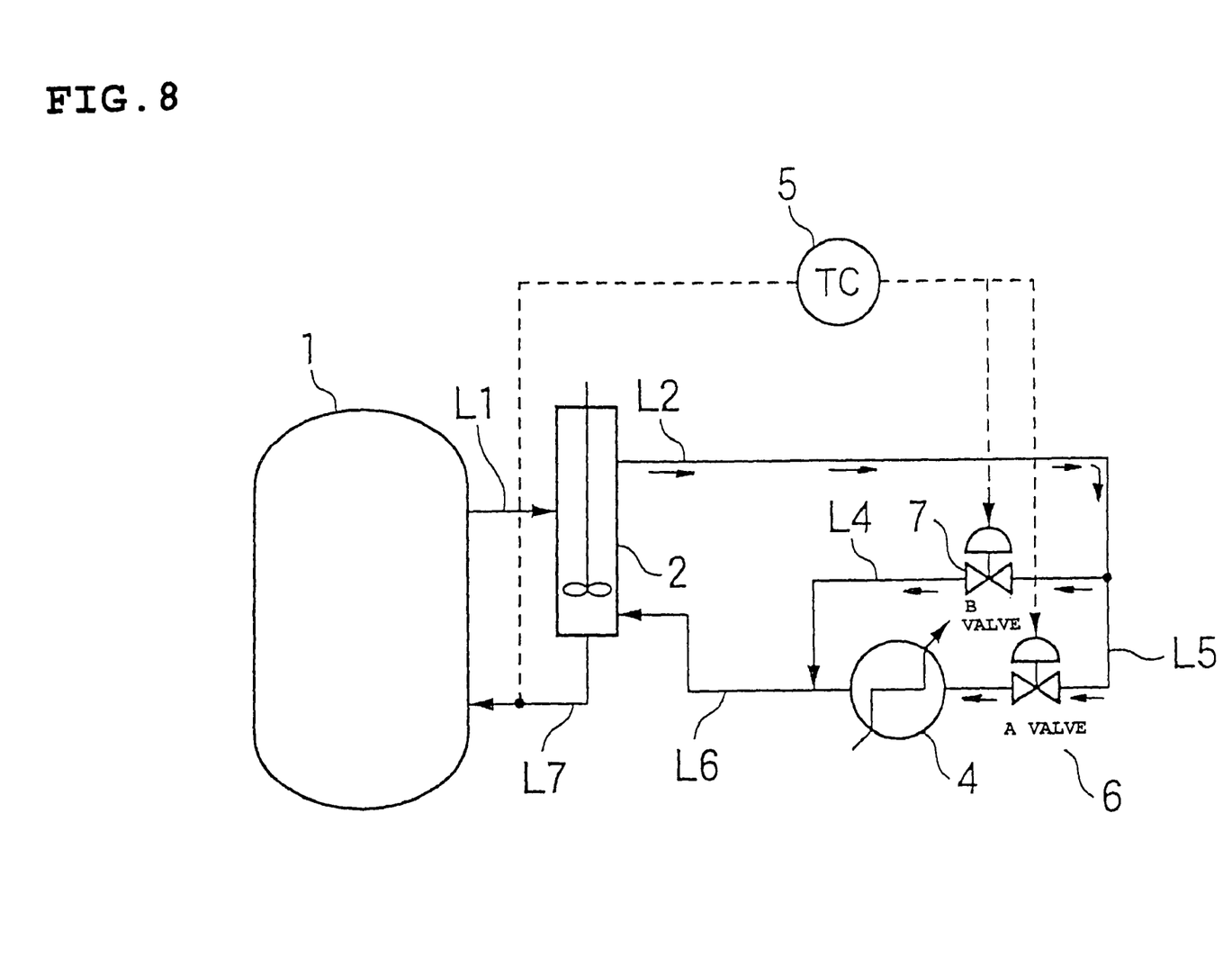
FIG. 8 is a conceptual view of multi-tubular reactor.

Indeed, FIG. 8 illustrates the multi-tubular reactor 1, at least one cooling apparatus 4 outside the reactor, a flow control valve 6 for supplying at least a part of the heat medium to the cooling apparatus, and a flow control valve 7 which bypasses the cooling apparatus.

This application is based on Japanese patent application filed on May 27, 2004 (Patent Application No. 2004-158036), the entire contents thereof being hereby incorporated by reference.

INDUSTRIAL APPLICABILITY

In accordance with the invention, provided is a multi-tubular reaction apparatus and a control system for the same, the multi-tubular reaction apparatus being capable of controlling change in temperature of a heat medium, quickly adjusting fluctuation in temperature, and thereby, properly performing reaction. When the multi-tubular reaction apparatus and the control system for the same in accordance with the invention are applied in producing (meth)acrylic acid from propane, propylene or isobutylene in a catalytic gas-phase oxidation method, for example, change in temperature of a heat medium can be controlled and fluctuation in temperature can be quickly adjusted even in the case of changing a condition such as change in amount of supplying raw material, so that a runaway reaction or early deterioration of a catalyst can be prevented, and thereby, stable production with a high yield can be achieved for a long term.

The precision necessary to the temperature control required in the case such as producing (meth)acrylic acid from propane, propylene or isobutylene is typically 0.2 to 1° C. It is quite difficult to control a temperature of the heat medium, which is massively circulated, in one step with such a precision. Nevertheless, temperature control of the heat medium with high precision can be achieved by using a reaction apparatus in accordance with the invention in which a heat medium taken out outside a shell is once cooled to a reference temperature, a part of the heat medium cooled to the reference temperature is further cooled and the heat medium cooled to the reference temperature is mixed with the heat medium further cooled under good temperature control.

The invention claimed is:

1. A multi-tubular reaction apparatus comprising:
   a shell,
   a plurality of reaction tubes provided in the shell and filled with a catalyst;
   a heat medium that circulates in the shell; and
   a cooling apparatus provided outside the shell, the cooling apparatus comprising,
   a primary cooler to cool at least a part of the heat medium taken outside the shell;
   a secondary cooler to cool at least a part of the primarily cooled heat medium;
   a flow control mechanism to divert a first fraction of the heat medium taken outside the shell into the secondary cooler and to by pass a second fraction of the heat medium taken outside the shell around the secondary cooler; and
   a return line connected to an output of the primary cooler and an output of the secondary cooler for enabling the secondarily cooled heat medium and a residual part of the primarily cooled heat medium, which is not secondarily cooled, to circulate in the shell.

2. The multi-tubular reaction apparatus according to claim 1, further comprising:
   a reaction apparatus control system to adjust a temperature of the heat medium circulating in the shell by adjusting the flow in the heat medium return line of the secondarily cooled heat medium and the residual part of the primarily cooled heat medium, which is not secondarily cooled, on the basis of a temperature of at least one point selected from a heat medium temperature in the shell and a catalyst temperature.

3. The multi-tubular reaction apparatus according to claim 2, wherein the flow control mechanism comprises:
   a flow control valve provided in a supply line connected from the primary cooler to the secondary cooler for supplying at least a part of the primarily cooled heat medium to the secondary cooler; and
   a flow control valve provided in a bypass line connected from the output of the primary cooler to bypass the secondary cooler, wherein the control valves are adjusted in opposite directions in adjusting a temperature of the heat medium circulating in the shell.

4. A catalytic gas-phase oxidation reaction method using the multi-tubular reaction apparatus according to claim 3, the method comprising:
   performing a catalytic gas-phase oxidation reaction by controlling a temperature using the reaction apparatus control system in the multi-tubular reaction apparatus.

5. A system for controlling a reaction apparatus comprising:
   a multi-tubular reactor, which further comprises a shell, a plurality of reaction tubes provided in the shell and filled with a catalyst, and a heat medium that circulates in the shell;
   at least one cooling apparatus to cool the heat medium, the cooling apparatus provided outside the reactor;
   a flow control valve provided in a line for supplying at least a part of the heat medium having been taken out outside the shell to the at least one cooling apparatus to cool the heat medium; and
   a flow control valve provided in a line of the heat medium, to bypass the cooling apparatus for the heat medium, wherein the flow control valves are used for adjusting a temperature of the heat medium circulating in the shell.

* * * * *